(12) United States Patent
De Beule

(10) Patent No.: US 10,290,487 B2
(45) Date of Patent: May 14, 2019

(54) TRANSMISSION WINDOW FOR A VACUUM ULTRAVIOLET GAS DISCHARGE LAMP

(71) Applicant: International Iberian Nanotechnology Laboratory, Braga (PT)

(72) Inventor: Pieter De Beule, Braga (PT)

(73) Assignee: International Iberian Nanotechnology Laboratory (PT)

( * ) Notice: Subject to any disclaimer, the term of this patent is extended or adjusted under 35 U.S.C. 154(b) by 902 days.

(21) Appl. No.: 14/779,926

(22) PCT Filed: Mar. 26, 2014

(86) PCT No.: PCT/EP2014/056020
§ 371 (c)(1),
(2) Date: Sep. 24, 2015

(87) PCT Pub. No.: WO2014/154730
PCT Pub. Date: Oct. 2, 2014

(65) Prior Publication Data
US 2016/0049288 A1 Feb. 18, 2016

(30) Foreign Application Priority Data
Mar. 27, 2013 (EP) ..................................... 13161391

(51) Int. Cl.
| | |
|---|---|
| *H01J 61/02* | (2006.01) |
| *G01N 27/66* | (2006.01) |
| *H01J 61/76* | (2006.01) |
| *H01J 61/30* | (2006.01) |
| *H01J 61/35* | (2006.01) |

(52) U.S. Cl.
CPC ............. *H01J 61/025* (2013.01); *G01N 27/66* (2013.01); *H01J 61/302* (2013.01); *H01J 61/35* (2013.01); *H01J 61/76* (2013.01)

(58) Field of Classification Search
None
See application file for complete search history.

(56) References Cited

U.S. PATENT DOCUMENTS

| | | | |
|---|---|---|---|
| 5,393,979 A | 2/1995 | Hsi | |
| 6,646,444 B2 | 11/2003 | Dolgov et al. | |
| 2007/0114395 A1 | 5/2007 | Swenson et al. | |
| 2013/0115423 A1* | 5/2013 | Ii | ............................. B05D 5/00 |
| | | | 428/141 |
| 2013/0146860 A1* | 6/2013 | Toyama | .............. H01L 51/0097 |
| | | | 257/40 |

FOREIGN PATENT DOCUMENTS

| | | |
|---|---|---|
| CN | 1 854 761 A | 11/2006 |
| DE | 10 2006 043407 A1 | 3/2008 |
| EP | 2 148 194 A1 | 1/2010 |
| RU | 2 129 319 C1 | 4/1999 |

* cited by examiner

*Primary Examiner* — Ashok Patel
(74) *Attorney, Agent, or Firm* — Condo Roccia Koptiw LLP

(57) ABSTRACT

A transmission window (1) for a VUV gas discharge lamp is defined which comprises a substrate (3) which is transparent to the VUV spectrum and a nanolayer stack (2) provided on the substrate, the nanolayer stack (2) comprising at least one nanolayer and the top layer of the nanolayer stack being electrically conducting. Also, a VUV gas discharge lamp, a photo-ionization device and a photo-ionization detector comprising said transmission window are defined.

20 Claims, 3 Drawing Sheets

TRANSMISSION WINDOW FOR A VACUUM ULTRAVIOLET GAS DISCHARGE LAMP

CROSS-REFERENCE TO RELATED APPLICATIONS

This application is the national phase entry under 35 U.S.C. § 371 of Patent Cooperation Treaty (PCT) Application No. PCT/EP2014/056020, filed Mar. 26, 2014, which claims the benefit of European Patent Application No. 13161391.1, filed Mar. 27, 2013, the contents of which are incorporated by reference herein.

TECHNICAL FIELD OF THE INVENTION

The present invention pertains generally to measuring and testing devices and more particularly to photo-ionization detectors. The present invention relates to a transmission window for a vacuum ultraviolet gas discharge lamp and to a VUV gas discharge lamp comprising the transmission window.

BACKGROUND OF THE INVENTION

Atmospheric Pressure Photo-ionization (APPI) is a well-known soft ionization mechanism, which induces the formation of electron-ion pairs from molecules upon the absorption of high energy photons without disintegrating the molecules into multiple fragments. The lowest binding energy of an electron to a molecule, also known as the first Ionization Potential (IP), typically lies within the range of 5 to 25 eV. Hence, high energy photons are required to ionize molecules. These photons are normally created by a low-pressure gas discharge lamp that, depending on the gas fill, typically emits intense light between 105 nm (11.8 eV) and 150 nm (8.4 eV). At these wavelengths, light is commonly referred to as vacuum ultraviolet (VUV) because it is absorbed by air.

Documents U.S. Pat. Nos. 5,393,979 and 6,646,444 disclose photo-ionization detectors according to the state of the art.

Typical applications of APPI include trace gas analysis through the combination of APPI with mass spectrometry, ion mobility spectrometry and liquid or gas chromatography. These applications are made possible through the convenient fact that the IPs of most carrier gasses and carrier liquids lie above the photon energy of VUV lamps. They are thus unaffected by a VUV radiation source, because the energy of the radiation is too low to cause ionization of these constituents. For example, the IPs of water (12.6 eV), acetonitrile (12.2 eV), nitrogen (14.5 eV) and helium (23 eV) are all considerably greater than the photon energies of VUV lamps with low pressure gas fills composed of xenon (8.4 and 9.6 eV), hydrogen (4.9 eV), deuterium (10.2 eV), krypton (10.6 eV) or argon (11.8 eV). Most organic molecules on the other hand exhibit IPs between 7 and 10.5 eV, making VUV lamps ideal devices to detect a wide variety of molecular compounds.

VUV lamps are divided in two categories depending on the electric field used to excite the low pressure gasses, i.e. lamps excited with DC electric fields and lamps driven by radio frequency (RF) electric fields. Lamps operated with DC fields comprise a metallic cathode and anode within a gas filled glass enclosure between which a high voltage of around 1 kV is applied to start the VUV generating discharge. These lamps are most commonly used in gas chromatography and tend to create a narrow and focused output beam. On the other hand, lamps driven by RF frequencies comprise a transparent glass enclosure containing the low pressure gas and can be further divided in subcategories depending on the coupling of RF power to the low pressure gas container of the VUV lamp, i.e. capacitively or inductively. RF VUV lamps exhibit higher energy efficiency than DC VUV lamps and are therefore the preferred VUV photon source for portable gas detectors. In contrast with DC lamps, they tend to emit an unfocussed collimated light beam.

Common silicon based glasses do not transmit VUV. Hence, the VUV transmission window is a crucial component of VUV lamps. Magnesium fluoride ($MgF_2$) and lithium fluoride (LiF) crystals are widely used materials for these transmission windows. $MgF_2$ is a material frequently used in infrared (IR) optics, but it also transmits UV light down to 110 nm. $MgF_2$ is also known as a rugged material resistant to chemical etching, laser damage, and mechanical and thermal shock. This makes it the transmission window material of choice for most VUV lamps. One notable exception is the high energy VUV lamp based on argon, which requires LiF crystals as VUV lamp window because a sufficiently high transmission coefficient for light below 110 nm is required. However, LiF has several disadvantages. First of all, LiF is a highly hygroscopic material, i.e. it disintegrates upon contact with highly humid environments. This is a major contributing factor to the short operational lifetimes, sometimes down to 100 hours, of argon based VUV lamps. A second major disadvantage of LiF is the incompatibility of its thermal expansion coefficient with ordinary glass, thus making it very hard to obtain a good seal, which is absolutely necessary to avoid the ingress of contamination or water in the glass enclosure of the lamp.

Continuous APPI effected with the VUV lamps described above results in a gradual reduction of the lamp transmission efficiency of the VUV lamp windows. This is mainly attributed to the adhesion of hydrocarbons to the lamp window [A. I. Vangonen et al., "Methods to increase the transmission of MgFI windows," *Soviet Journal of Optical Technology*, vol. 55, no. 11, pp. 672-674, 1988]. Nanometer thick attachments of hydrocarbons are sufficient to cause a significant drop in VUV intensity. This phenomenon can be partly solved by cleaning the lamp window with methanol. However, operation of the VUV lamp in high concentrations of volatile organic compounds can create such an intense deposition of hydrocarbons on the lamp window that cleaning with methanol does not suffice any longer and a treatment with high purity alumina ($Al_2O_3$) particles or fine diamond polish becomes necessary. Such cleaning procedures eventually lead to the gradual degradation and eventual destruction of the lamp window.

It is an object of the invention to provide a transmission window which provides prolonged operational lifetime of the VUV gas discharge lamp while maintaining the transmission efficiency in the VUV range. Other objects and advantages of the invention will be explained below.

SUMMARY OF THE INVENTION

The present invention presents a transmission window for a VUV gas discharge lamp according to claim 1, a VUV gas discharge lamp according to claim 13, a photo-ionization device according to claim 14 and a photo-ionization detector according to claim 15. Dependent claims define preferred embodiments of the invention.

In a first aspect, a transmission window for a VUV gas discharge lamp is defined. The transmission window comprises a VUV-transparent substrate, i.e. substrate which is transparent to the VUV spectrum, and a nanolayer stack provided on the substrate. The nanolayer stack comprises one or several nanolayers, and the top layer of the nanolayer stack is electrically conducting.

Advantageously, the transmission window of the invention allows its use in a photo-ionization detector without requiring the placement of a cupper electrode on the top. This results in a smaller size required for the sample ionization volume and in enhanced transmission of VUV light, as will be shown below in more detail.

Throughout the application a nanolayer shall be construed as a layer having a thickness in the nanoscale range. For simplicity, the term layer will be used as a synonym of nanolayer for the nanolayers of the stack.

The top layer of the stack will be understood as the layer of the stack the most distant from the substrate. The inner layer of the stack will be understood as the layer of the stack closest to the substrate. Where only one layer is included in the stack, it will be understood to be both the inner and top layer of the stack.

In a preferred embodiment, the top layer of the stack is made of a conducting and inert material. Advantageously, use of an inert material in the top layer reduces the interaction of the gas analyte ionization process with the transmission window, thus resulting in fewer deposits being formed.

The transmission window according to the invention prolongs the operational lifetime of the VUV lamp by reducing the attachment of hydrocarbon contaminants on the VUV lamp window. Also, the integrity over time of argon based VUV lamps with highly hygroscopic lithium fluoride crystals is improved.

In a preferred embodiment the top layer is made of a metal, preferably a noble metal, such as ruthenium, rhodium, palladium, silver, osmium, iridium, platinum and gold, or of an alloy of noble metals. Advantageously, noble metals are resistant to corrosion and oxidation in moist air.

$MgF_2$ or LiF crystals are preferred for the substrate of the transmission window.

Where the top layer provides an adequate bonding to the substrate, it can be directly deposited on the substrate, i.e. with no intermediation of additional means, thus providing a nanolayer stack containing only one nanolayer. On the other hand, where the nature of the substrate and the top layer does not provide an adequate direct bonding, a bonding layer may be included as an inner layer of the nanolayers stack to provide a physical bonding between the top layer of the nanolayers stack and the substrate.

In a preferred embodiment, the thickness of the nanolayer stack is comprised in the range from one atomic monolayer to 20 nm. Advantageously, by providing a stack of nanolayers with such a thickness, the chemical and physical properties of the lamp window surface are modified with no considerable reduction of the transmission efficiency in the VUV range.

In a preferred embodiment, the nanolayer stack comprises only two nanolayers, each made of a different material.

In a preferred embodiment, the thickness of the each layer of the nanolayers stack is comprised in the range from 1 to 10 nm, more preferably in the range from 1 to 3 nm.

In a preferred embodiment, the top layer is made of gold, which is both an inert and conducting material. Preferably, the thickness of the gold layer is comprised in the range from 1 to 3 nm. One or more additional layers of different materials may be also included in the stack.

In a preferred embodiment, the substrate is a $MgF_2$ or a LiF crystal and the stack includes only two layers: an inner bonding layer and a top layer of a noble metal provided thereon. The noble metal is preferably gold. The bonding layer is preferably made of chromium, nickel-chromium, titanium or molybdenum. Advantageously, a bonding layer made of such materials enhances the adherence of the noble metal layer to the substrate, thus assuring the physical bonding of the gold layer to the substrate. Preferably, the thickness of each layer is comprised in the range from 1 to 10 nm, more preferably in the range from 1 to 3 nm.

In a preferred embodiment, the top layer comprises at least two regions, each made of a different material, the regions being electrically isolated from one another. The isolation of the regions may be provided by the inclusion of an insulating barrier between the regions, the isolating barrier been made of an isolating material deposited between the regions. Additionally or alternatively, the isolation may be provided by an empty isolation region in which no material has been provided. Preferably, the two regions are made each of a noble metal.

In a preferred embodiment of the top layer comprising at least two regions, the top layer includes a first region made of gold and a second region made of silver.

In a second aspect, the invention defines a VUV gas discharge lamp comprising a glass enclosure containing a low pressure gas and a VUV transmission window according to the first aspect of the invention. The transmission window is placed in the VUV lamp with the nanolayers stack towards the exterior of the lamp, such that the side of the transmission window exposed to the species to be detected is the side provided with the nanolayers stack.

In a third aspect, the invention defines a photo-ionization device comprising a VUV lamp according to the second aspect, and excitation means capable to excite the low pressure gas contained in the glass enclosure of the VUV lamp. Preferred excitation means are those capable of generating RF power and/or DC electric fields.

In a forth aspect, the invention defines a photo-ionization detector comprising a photo-ionization device according to the third aspect, a sample ionization volume exposed to the VUV lamp transmission window of the photo-ionization device, a first electrode located within the sample ionization volume for capturing ionized sample molecules, means for applying a voltage between the first electrode and a second electrode and means for measuring the current between the first and the second electrode resulting from ionization of sample molecules flowing therebetween. Advantageously, the top conducting layer of the nanolayer stack may be used as the second electrode, thus avoiding the requirement to use an additional electrode. Use of the top conducting layer of the nanolayer stack as the second electrode results in greater transmission efficiency compared to the case where a commercial electrode is placed on the transmission window and also allows reducing the ionization volume of the photo-ionization detector, which reduces in turn the response time for the detection of volatile organic compounds. Notwithstanding the above, an additional electrode located in the sample ionization volume may still be used as the second electrode if required in a particular case.

All the features described in this specification (including the claims, description and drawings) and/or all the steps of the described method can be combined in any combination, with the exception of combinations of such mutually exclusive features and/or steps.

BRIEF DESCRIPTION OF THE DRAWINGS

To better understand the invention, its objects and advantages, the following figures are attached to the specification in which the following is depicted:

FIG. 5 shows the applied Toluene concentration as a function of time and FIG. 6 shows the absolute photo-ionization detector response to the Toluene concentration applied.

PREFERRED EMBODIMENTS OF THE INVENTION

Figure 1:
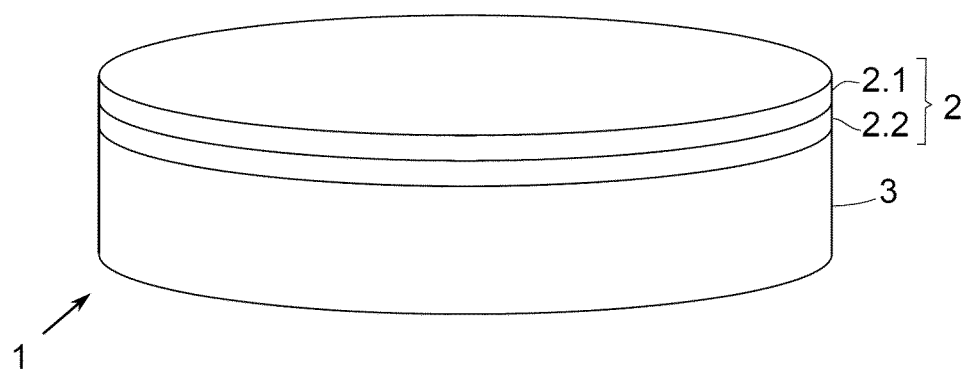
FIG. 1 shows a transmission window according to an embodiment of the invention.

FIG. 1 shows a transmission window (1) for a VUV gas discharge lamp according to an embodiment of the invention. The transmission window (1) comprises a substrate (3) which is transparent to VUV radiation and a stack of layers (2) provided on the substrate. In this embodiment the stack of layers includes two nanolayers (2.1, 2.2), the inner layer (2.2) being made of chromium and the top layer (2.1) being made of gold. The stack of nanolayers can be provided on the substrate by conventional thin film deposition technologies, for example with sputter deposition technology.

In the embodiment depicted the stack only includes two nanolayers. However, a multilayer stack having more than two layers of different materials may be provided in a different embodiment. Also, a stack of nanolayers including only one nanolayer may be provided in a different embodiment.

The thickness of the stack of nanolayers is preferably less than 20 nm.

In the embodiment of FIG. 1 the transmission window comprises a $MgF_2$ substrate (3) coated with a 2.5 nm chromium layer (2.2) and a 2.5 nm gold layer (2.1) provided thereon. In this case, the chromium layer (2.2) enhances the physical bonding between the substrate and the gold layer (2.1).

Figure 2:
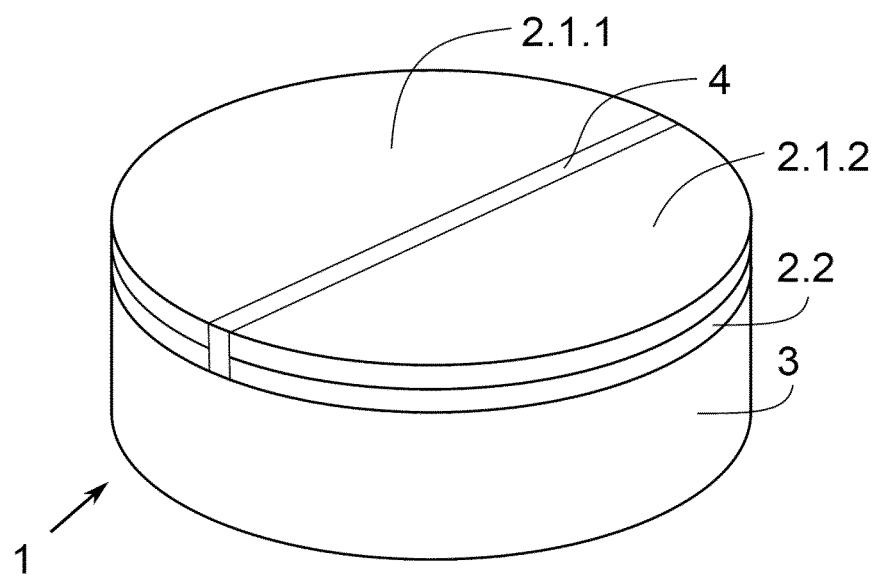
FIG. 2 shows a transmission window according to a second embodiment of the invention.

FIG. 2 shows a transmission window according to an embodiment of the invention. In this embodiment an inner layer (2.2) and an top layer are provided on the substrate (3), wherein the top layer comprises two regions (2.1.1, 2.1.2), each made of one conducting material, such as silver (2.1.1) and gold (2.1.2). The regions (2.1.1, 2.1.2) of the top layer are electrically insulated from one another by insulating means (4), which in the embodiment of FIG. 2 are provided in the form of an insulating barrier. In the embodiment shown the inner layer (2.2) is made of chromium and the substrate is made of $MgF_2$ or LiF.

Figure 3:
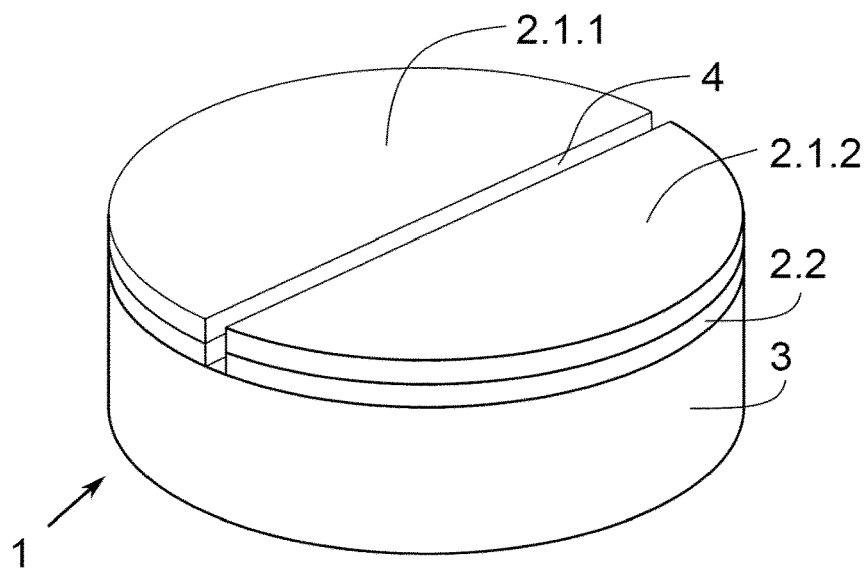
FIG. 3 shows a transmission window according to a third embodiment of the invention.

FIG. 3 shows a transmission window according to another embodiment of the invention. As in the embodiment depicted in FIG. 2, two nanolayers (2.1, 2.2) are provided on a substrate (3), top layer comprising two regions (2.1.1, 2.1.2), each made of one conducting material, such as silver (2.1.1) and gold (2.1.2). In this embodiment the insulating means (4) electrically insulating the two regions (2.1.1, 2.1.2) of the top layer are provided in the form of an empty space with no coating provided.

Advantageously, with the transmission window according to the embodiments of FIGS. 2 and 3, two contacts may be connected to each region of the top layer (2.1), i.e. to the silver and gold regions of the example, which allows to determine a resistance value for each region. The resistance value of each region will vary differently depending on the gas exposed to the region, hereby offering a way to differentiate between the gases to be detected. As a simple example, given two substances A and B to be detected, both giving the same photo-ionization detector response and being hence indistinguishable, where the resistivity of each region of the transmission window top layer is differently affected when exposed to substance A or B (for example, substance A raises both the resistivity of the first and second regions, while substance B raises the resistivity of the first region and lowers the resistivity of the second region), a transmission window according to this embodiment makes substances A and B distinguishable.

The above embodiment is not limited to the top layer having two isolated regions made of different conducting materials. In a preferred embodiment a plurality of isolated regions are provided in the top layer, each region being made of a different material. Where the resistivities of the materials of the top layer regions behave differently with respect to different gases, the incoming gas will be distinguishable based on the analysis of the change in the resistivity of each material due to the presence of the gas being detected, which is not possible with current photo-ionization detection technology. Thus, a photo-ionization detector according to this embodiment, i.e. provided with a transmission window of the VUV lamp having at least two isolated regions made of different conducting materials in the top layer of the nanolayers stack, provides additional capabilities to distinguish detected substances.

Figure 4:
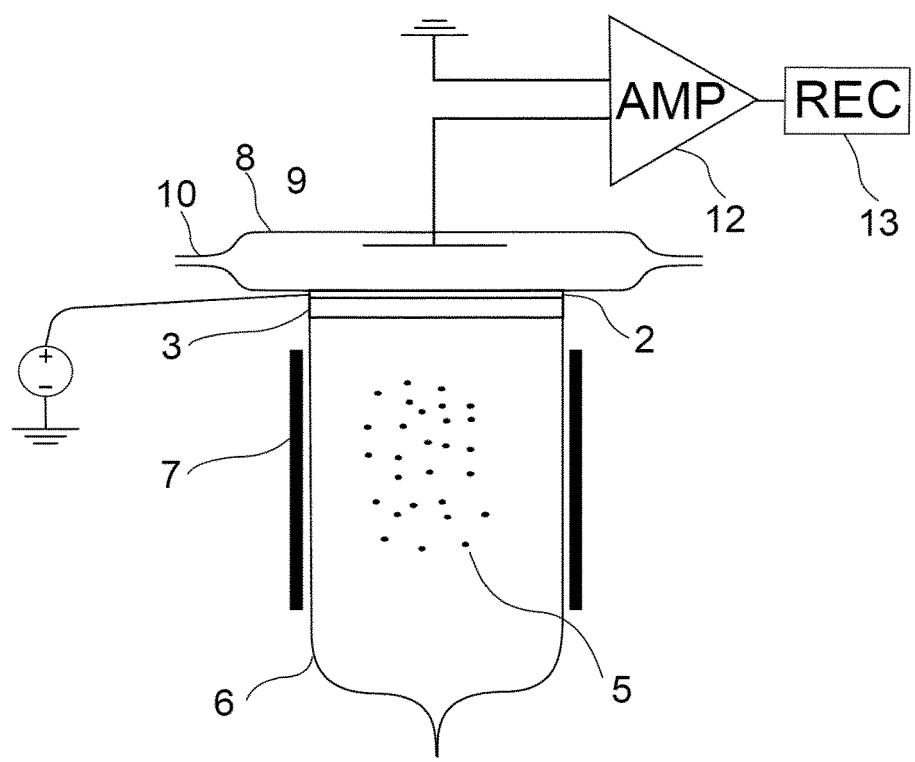
FIG. 4 shows a photo-ionization detector according to the invention.

FIG. 4 depicts schematically a photo-ionization detector according to the invention. The photo-ionization detector comprises a VUV lamp according to the invention, in this case a lamp excited with inductively coupled RF, although DC excited lamps can be used as well. The VUV lamp comprises a glass enclosure (6), a low-pressure gas fill (5) and a VUV lamp transmission window (1) comprising a substrate (3), preferably made of $MgF_2$ or LiF crystal, and a nanolayer stack (2) exposed to a sample ionization volume. In this embodiment an inductive coupling of RF electric fields occurs with an antenna (7), which is used as the excitation means.

As mentioned, the photo-ionization detector additionally comprises a sample ionization volume, which in this example is a sample ionization chamber (8) having sample inlet (10) and sample outlet (11) means through which the sample to be analyzed enters and leaves the sample ionization chamber (8). An electrode (9) for capturing the ionized sample molecules is located within the sample ionization chamber (8). Since the top layer of the nanolayer stack (2) is electrically conducting, it is used as a second electrode. A voltage is applied between the first electrode and the top layer of the nanolayer stack (2) to create an electric field to separate the generated electron-ion pairs generated by the VUV lamp and the current resulting from the ionization of sample molecules is measured. An inverting transimpedance amplifier (12) converts the small ionic currents to a proportional voltage signal and a voltage recorder (13) registers the detected signal. Other options known by the skilled person are possible for the electronic detection circuitry.

Instead of using the conducting top layer of the nanolayer stack (2) as the second electrode, two electrodes may be provided within the sample ionization volume. Nevertheless, coupling an electronic voltage source to the conducting top layer of the nanolayer stack (2), as shown in the embodiment of FIG. 4, removes the requirement to introduce the second electrode in the sample ionization volume, which allows to reduce the volume of the sample ionization volume, thus lowering the lower concentration detection limit and reducing the detection response time.

The provision of a stack of nanolayers on the transmission window of VUV low pressure discharge lamps has a double advantage. The modification of the surface layer of the VUV lamp transmission window to a conducting and inert material, preferably a metal, such as gold, reduces the hydrocarbon contamination and hence prolongs the operational lifetime of the lamp. This comes at the cost of reduced VUV lamp output. However, since the VUV lamp comprising the transmission window of the invention does not require the use of an electrode placed thereon when arranged in a photo-ionization detection, the absence of the electrode compensates the reduction of the VUV output, as will be shown in the example below. Also, the reduction of the VUV lamp output due to the presence of the nanolayers stack can be further minimized by an appropriate choice of the nanolayers.

Figure 5:
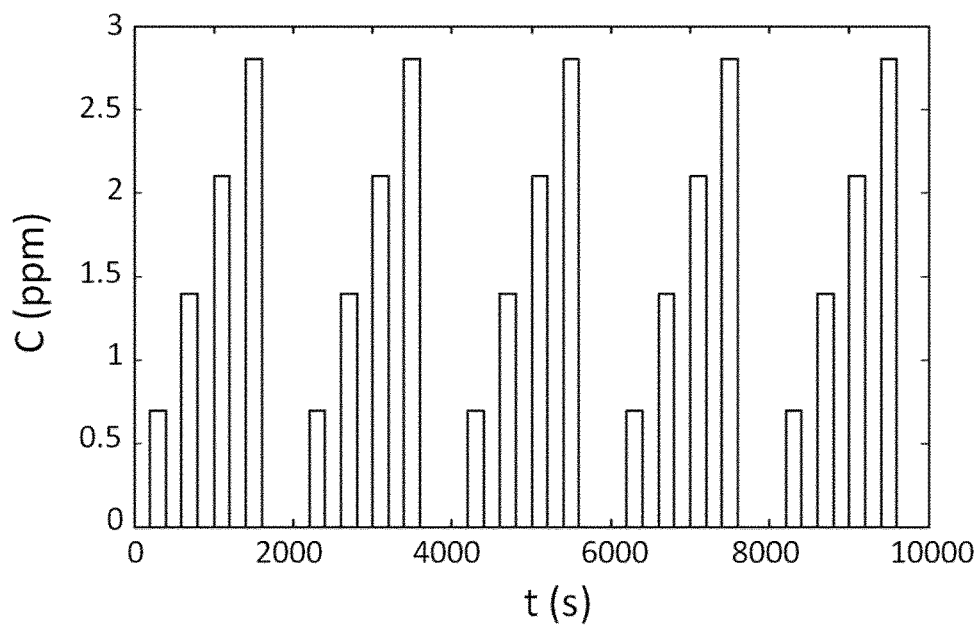
FIGS. 5 and 6 show an experiment in which a Toluene concentration is applied to a photo-ionization detector according to the invention.
Figure 6:
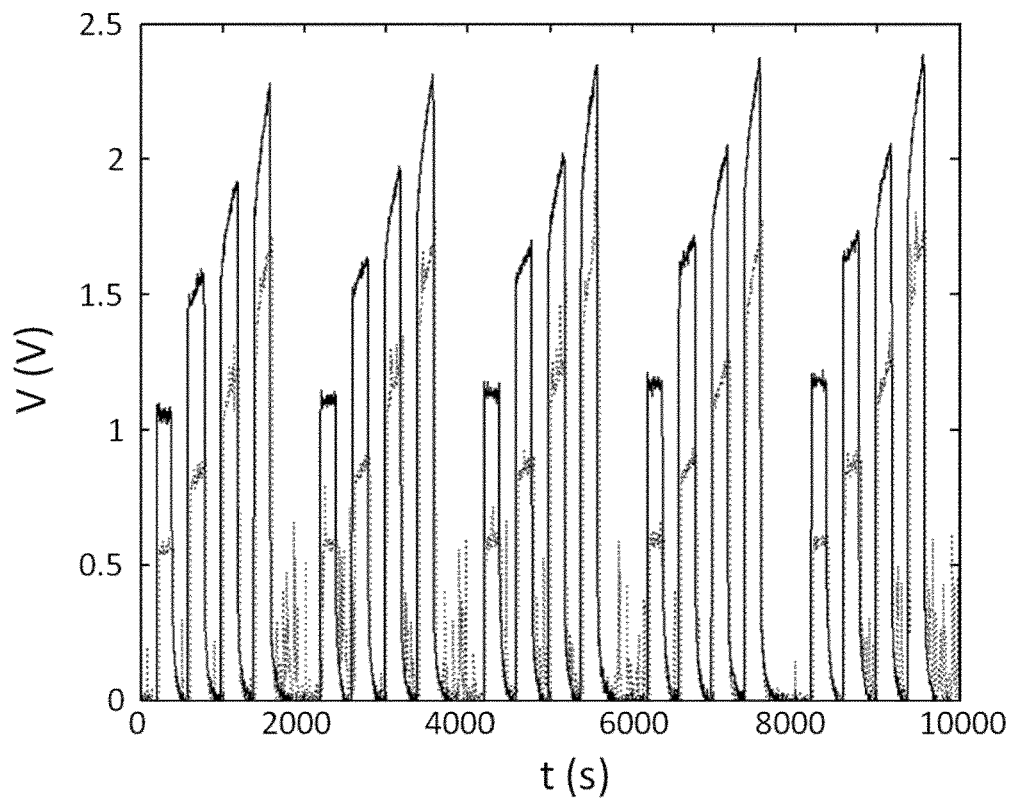

FIGS. 5 and 6 show the results of an experiment performed with a photo-ionization detector according to an embodiment of the invention and compared with a conventional photo-ionization detector according to the state of the art. In this experiment, the conventional photo-ionization detector comprises a Krypton lamp having a $MgF_2$ transmission window, whereas in the photo-ionization detector according to the invention the $MgF_2$ transmission window of the Krypton lamp is coated with a with a 2.5 nm inner Cr nanolayer and a 2.5 nm top Au nanolayer coated thereon.

FIG. 5 shows the toluene challenge applied to both photo-ionization detectors, where the concentration of toluene is plotted versus time. The toluene challenge was created by sampling the headspace of a bottle with toluene (i.e. saturated vapour pressure at laboratory temperature), diluted in different ratios to create the concentration profile shown in FIG. 5.

FIG. 6 shows the absolute photo-ionization detector response after background subtraction for the conventional photo-ionization detector (solid line) and for the photo-ionization detector according to the invention, comprising a transmission window provided with a nanolayer stack (dotted line). The voltage response of the photo-ionization detector (integrated transimpedance value of the ionization current) is plotted on the same timescale as the toluene challenge of FIG. 5. The results depicted in FIG. 6 indicate that the transmission window provided with the 2.5 nm Cr/2.5 nm Au nanolayer stack transmits approximately 62% of the VUV light generated at 10.6 eV, the energy of the light emitted by a Kr lamp.

Since the top layer of the nanolayer stack may be used as an electrode, as previously discussed, the photo-ionization detector of the invention does not require the use of an additional electrode, whereas with a photo-ionization detector according to the state of the art, it is essential to have an electrode placed on the transmission window of the VUV lamp. An electrode of the type to be placed on the transmission window of a VUV lamp contains holes for the transmission of the VUV radiation. When the electrode is placed covering the transmission window, the VUV light is transmitted only through the electrode holes, which significantly reduces the transmission efficiency of the transmission window. Accordingly, the VUV transmission efficiency of the transmission window of the invention (62% in the present example) should be compared to the transmission efficiency of the conventional transmission window taking into consideration the relative size of the holes in a physical electrode with respect to the total surface area of the lamp transmission window. For typical commercial electrodes the transmission efficiency of the transmission window provided with the electrode is approximately 26%.

Consequently, in the experiment performed, the VUV transmission efficiency of the transmission window according to this embodiment of the invention is 62% with no further reduction due to the presence of an electrode, whereas in the photo-ionization detector according to the state of the art the final VUV transmission efficiency is approximately 26%.

The prime application area of the present invention is for use within portable threat detectors for volatile potentially hazardous organic compounds, where the VUV lamp tends to be exposed to a large variety of unknown compounds. Degradation of the VUV lamp, due to the degradation of its transmission window, represents a real limitation for such an application, not only because lamp replacement becomes necessary after a limited amount of operating hours, but also because the non-detection of a compound can be attributed to the non-presence of a threat or the presence of a threat in combination with a non-functional lamp. Also, the replacement or cleaning of VUV lamps on field operations is not always possible.

The invention may be used in an ion detection scheme different from the one presented, such as for example Ion Mobility Spectrometry (IMS), Mass Spectrometry (MS), Gas Chromatography (GC) or liquid chromatography (LC). These techniques can further discriminate between compounds and better analyze gas mixtures as compared to photo-ionization detectors. In these embodiments, a photo-ionization device provided with a transmission window according to the invention will provide the same advantages already stated of prolonging operational lifetime while maintaining the transmission efficiency in the VUV range. It should be noted that, if the compound under investigation is known beforehand, a photo-ionization detector can be calibrated to report the concentration of the compound present, whereas IMS, MS, GC and LC add another layer of information to the data collected about the gaseous or liquid sample, since they can discriminate between compounds.

The invention claimed is:

1. A vacuum ultraviolet (VUV) gas discharge lamp comprising:
   a glass enclosure containing a low pressure gas; and
   a VUV transmission window, wherein the VUV transmission window comprises:
   a VUV-transparent substrate, and
   a nanolayer stack adjacent to the VUV-transparent substrate wherein the nanolayer stack comprises at least one nanolayer, and at least a top nanolayer of the nanolayer stack is conductive,
   wherein the top nanolayer comprises at least two regions, the at least two regions comprise a first region and a second region, the first region is comprised of a first conductive material, the second region is comprised of a second conductive material, the first and second conductive materials are different, and the first and second regions are electrically isolated from one another.

2. The VUV gas discharge lamp according to claim 1, wherein the top nanolayer of the nanolayer stack is comprised of an inert material.

3. The VUV gas discharge lamp according to claim 1, wherein a thickness of the nanolayer stack is comprised in the range from one atomic monolayer to 20 nm.

4. The VUV gas discharge lamp according to claim 1, wherein the nanolayer stack comprises two nanolayers.

5. The VUV gas discharge lamp according claim 1, wherein the nanolayer stack comprises at least two nanolayers, the at least two nanolayers are comprised of the top nanolayer and a bottom nanolayer, the top nanolayer comprises a first material, the bottom layer is comprised of a second material, and the first and second materials are different materials.

6. The VUV gas discharge lamp according to claim 1, wherein the top nanolayer is comprised of at least one of a noble metal or of an alloy of a noble metal.

7. The VUV gas discharge lamp according to claim 1, wherein the thickness of the each nanolayer included in the nanolayer stack is comprised in the range from 1 to 3 nm.

8. The VUV gas discharge lamp according to claim 1, wherein the nanolayer stack comprises an inner bonding layer provided on the substrate, the inner bonding layer being configured to enhance the adherence of the nanolayer stack to the substrate.

9. The VUV gas discharge lamp according to claim 8, wherein the inner bonding layer is comprised of one or more of chromium, nickel-chromium, titanium, or molybdenum.

10. The VUV gas discharge lamp according to claim 1, wherein the first and second regions are electrically isolated from one another by an empty isolation region, wherein the empty isolation region is configured to provide electric isolation by being devoid of material.

11. The VUV gas discharge lamp according to claim 10, wherein the first region is comprised of a first noble metal, and the second region is comprised of a second noble metal.

12. The VUV gas discharge lamp according to claim 11, wherein the first noble metal is gold and the second noble metal is silver.

13. The VUV gas discharge lamp according to claim 1, wherein the first and second regions are electrically isolated from one another by an empty isolation region, wherein the empty isolation region is configured to provide electric isolation by including an electrically isolating material between the first and second regions.

14. The VUV gas discharge lamp according to claim 13, wherein the first region is comprised of a first noble metal, and the second region is comprised of a second noble metal.

15. The VUV gas discharge lamp according to claim 14, wherein the first noble metal is gold and the second noble metal is silver.

16. The VUV gas discharge lamp according to claim 1, wherein the first and second regions are electrically isolated from one another by an empty isolation region, wherein empty isolation region is configured to provide electric isolation by being devoid of material and by including an electrically isolating material between the first and second regions.

17. The VUV gas discharge lamp according to claim 16, wherein the first region is comprised of a first noble metal, and the second region is comprised of a second noble metal.

18. The VUV gas discharge lamp according to claim 17, wherein the first noble metal is gold and the second noble metal is silver.

19. Photo-ionization device, comprising:
a glass enclosure containing a low pressure gas;
a VUV transmission window, wherein the VUV transmission window comprises:
a VUV-transparent substrate, and
a nanolayer stack adjacent to the VUV-transparent substrate, wherein the nanolayer stack comprises at least one nanolayer, and at least a top nanolayer of the nanolayer stack is conductive, wherein the top nanolayer comprises at least two regions, the at least two regions comprise a first region and a second region, the first region is comprised of a first conductive material, the second region is comprised of a second conductive material, the first and second conductive materials are different, and the first and second regions are electrically isolated from one another; and
an excitation device configured to excite the low pressure gas contained in the glass enclosure.

20. The photo-ionization device as in claim 19, further comprising:
a sample ionization volume exposed to the VUV lamp transmission window,
a first electrode located in the sample ionization volume, the first electrode being configured to capture ionized sample molecules,
a voltage source configured to apply a voltage between the first electrode and a second electrode, and
a current measurement device configured to measure a current between the first and the second electrode resulting from ionization of sample molecules in the sample ionization volume, wherein the second electrode is located in one of the top nanolayer of the nanolayer stack or in the sample ionization volume.

* * * * *